United States Patent [19]
von Knebel-Doeberitz et al.

[11] Patent Number: 6,051,382
[45] Date of Patent: Apr. 18, 2000

[54] PROCESS FOR RECOGNIZING THE RISK OF BECOMING ILL AFTER AN ARTHROPOD BITE

[75] Inventors: Magnus von Knebel-Doeberitz; Matthias Maiwald, both of Heidelberg, Germany

[73] Assignee: Deutsches Krebsforschungszentrum Stiftung Des Offentlichen Rechts, Heidelberg, Germany

[21] Appl. No.: 09/125,253

[22] PCT Filed: Feb. 14, 1997

[86] PCT No.: PCT/DE97/00311

§ 371 Date: Jan. 27, 1999

§ 102(e) Date: Jan. 27, 1999

[87] PCT Pub. No.: WO97/30177

PCT Pub. Date: Aug. 21, 1997

[30] Foreign Application Priority Data

Feb. 14, 1996 [DE] Germany .............................. 196 05 475

[51] Int. Cl.[7] .................. C12Q 1/68; C12Q 1/70
[52] U.S. Cl. .................... 435/6; 435/5; 435/975; 536/24.32; 536/24.31
[58] Field of Search ................... 435/6, 975, 5; 536/24.32, 24.31

[56] References Cited

FOREIGN PATENT DOCUMENTS 0 421 725   of 0000   European Pat. Off. .

OTHER PUBLICATIONS

Shott S.R.: "Diagnosis and management of Lyme Disease", Current Opinion In Otolaryngology and Head and Neck Surgery, Bd. 3, Nr. 6, Dec. 1995, Seiten 379–382, XP002042421.

Peavey C.: "Transmission of Borellia Burgdorferi by Ixodes Pacificus" Journal of Parisitology, Bd. 81, Nr. 2, Apr. 1995, Seiten 175–8, XP002042422.

Schwartz J. et al., "Diagnosis of early Lyme disease by polymerase chain reaction amplification and culture of skin biopsies from Erythema Migrans lesions", J. Clin. Microbiol, BD. 30, Dec. 1992.

Kirstein et al, Applied and Environmental Microbiology 62:4060–4065, Nov. 1996.

Gokool et al, Med. Vet. Entomol 7:208–15, 1993, abstract only.

*Primary Examiner*—Mary E. Mosher
*Attorney, Agent, or Firm*—Burns, Doane, Swecker & Mathis, L.L.P.

[57] ABSTRACT

The present invention relates to a process for recognizing the risk of falling ill after an arthropod bite, which is characterized in that after the prick or bite of a host by an arthropod, nucleic acid of the host and nucleic acid of a pathogen passed along or onn by the arthropod are demonstrated to be present in the latter. Furthermore, the invention concerns a kit suited for the purpose of carrying out the process.

13 Claims, No Drawings

PROCESS FOR RECOGNIZING THE RISK OF BECOMING ILL AFTER AN ARTHROPOD BITE

This application is a 371 of PCT/DE97/00311, filed Feb. 14, 1997.

The present invention relates to the detection of a nucleic acid of a host bitten by an arthropod and a nucleic acid of an arthropod-borne pathogen in the arthropod. Furthermore, this invention concerns a kit suitable for carrying out the detection.

There are a plurality of arthropods world-wide, which attack human or animal hosts by a prick or bite. These arthropods transmit a plurality of pathogens, e.g. viruses, bacteria, protozoa or worms. The most widely known pathogen transmitted by arthropods, particularly ticks, is *Borrelia burgdorferi* which causes Lyme disease. The connections and courses of the bite by an arthropod, particularly tick, are explained below by means of the Lyme disease.

Lyme disease is a disease which is transmitted by tick bite and occurs in wide regions of the Northern hemisphere. In Central Europe and North America, it is the most frequent arthropod-borne disease. The rate of attack by ticks bearing the *Borrelia burgdorferi* pathogen varies according to the region. The U.S. report attack rates of up to 55%, while values of attack are reported to be between 2.5% and 36% for Europe.

Lyme disease proceeds in stage-like fashion. A tick bite initially causes a local infection (stage I; erythema migrans) with an incubation period of several days to few weeks, pathogen generalization occurs in the further course (stage II; symptoms at the nervous system, heart or joints), and an organ manifestation is found after months or years (stage III, late stage; Lyme arthritis or acrodermatitis chronica atrophicans). Individual disease stages can also be omitted or spontaneous healing may occur.

All in all, both clinical and laboratory diagnostics of Lyme disease are difficult and in some clinical cases accompanied by great uncertainty. Since the direct detection of the pathogen in patients' materials is regarded as unreliable, serological methods are usually used in support of diagnosis. In early disease stages, however, the antibody titers found are frequently not increased even though an infection has taken place, so that serology is sometimes no reliable criterion here. In some cases, this applies even to neuroborreliosis which may show a dangerous clinical picture and whose limitation over neurological diseases having a different cause is of great importance.

The Lyme disease is treated in accordance with the level of knowledge from stage II of the disease by intravenous administration of antibiotics. Such an administration requires either daily visits or the patient's hospitalization. The costs for the administered antibiotics presently amount to about 2500.—to 5000.—German marks per treatment cycle alone. In some cases, very aggressive disease processes are observed, which require several treatment cycles thus causing very high treatment costs.

Statements on the infection risk after tick bite are scanty so far and have usually been determined without reference to the positivity or negativity of the tick. U.S. investigations assume that 1 to 3% of tick bites in endemic regions result in an infection with *Borrelia burgdorferi*. In this connection, Magid et al., N. Engl. J. Med. 327, (1992), 534–541, draw the conclusion by way of statistical cost-benefit analysis that in regions highly contaminated with ticks bearing *Borrelia burgdorferi* it would be useful to administer prophylactically antibiotics after every tick bite. In Germany, antibiotic prophylaxis after tick bite is rejected. It is recommended instead to start a treatment in well-calculated fashion only if symptoms of Lyme disease occur. This recommendation is accompanied by two essential drawbacks: (1) Individual stages of the disease (e.g. erythema migrans) may be omitted, and the disease can start with symptoms of stage II or III which are difficult to diagnose and whose treatment is expensive. (2) If there is a reliable possibility of evaluating the infection risk soon after a tick bite, it can hardly be justified under ethical aspects to expose patients to the risk of a disease and the accompanying ailments. In addition to these drawbacks, an antibiotic prophylaxis or the treatment of an early infection can be carried out much easier and cheaper than the treatment of an infection at a later date.

Up to the present, there have hardly been any criteria of being able to evaluate reliably the disease risk for an individual host after individual arthropod prick or bite and derive an indication as to the prophylactic treatment therefrom. In the case of Lyme disease, the existing recommendations regarding the behavior after tick bite resulted from the fact that conventional detection methods for *Borrelia burgdorferi* in ticks, such as culture, dark-field microscopy or direct immunofluorescence, have no sufficient reliability. On the one hand, the cause of this is the low sensitivity of the methods and, on the other hand, the fact that blood constituents in ticks which have already begun to suck interfere with these detection methods considerably. Thus, up to the present it has not been possible by conventional methods to determine the infection risk resulting from a tick bite for those affected with sufficient security.

Therefore, it was the object of the present invention to provide a process by which, directly after an arthropod prick and bite, respectively, it is possible to evaluate, as accurately as possible, the risk for the affected host or patient to get an arthropod-borne disease and, as a function of the determined amount of risk, to carry out a prophylaxis, particularly by means of antibiotics.

According to the invention this is achieved by a process according to claim 1. Advantageous embodiments and a kit suitable for carrying out the process follow from the subclaims.

The process according to the invention is due to the applicant's finding that, based on a prick or bite by an arthropod, on the one hand, the arthropod absorbs constituents from the host and, on the other hand, arthropod constituents are passed on to the host. The constituents passed on to the host by the arthropod may also comprise the above-mentioned pathogens. Thus, it can be inferred by investigating the arthropod whether the latter has absorbed constituents from the host and simultaneously accommodates pathogens.

A nucleic acid from the host and that of an arthropod-borne pathogen in the arthropod are detected by common methods, preferably by means of PCR. For a PCR, the arthropod is removed from the host, and nucleic acid is isolated from the arthropod. It is amplified by using suitable primers for the host's nucleic acid and those for the nucleic acid of a pathogen, respectively, and the amplification products are detected, it being possible to carry out the individual steps separately or jointly. The infection risk for the host can safely be predicted by means of this diagnosis.

The expression "nucleic acid" comprises RNA and DNA, the expression "host" includes animals and human beings. Furthermore, the term "arthropods" covers insects, particularly ticks and mosquitos, spiders and crabs. In addition, the expression "pathogen" includes viruses, bacteria, protozoa and worms.

The detection of both nucleic acid sequences from the host and pathogen-specific nucleic acid sequences in the arthropod, optionally in combination, enables an evaluation of the disease risk after arthropod prick or bite, which is substantially more accurate than would be the case if conventional pathogen detection methods, such as culture or microscopy, were used or also if only nucleic acid of the pathogen was detected in the host.

The process according to the invention is described below by way of example to detect ticks bearing *Borrelia burgdorferi*, the pathogen of Lyme disease. This pathogen is usually found in the midgut of the ticks but not or only rarely in the saliva thereof. In a first stage following the tick bite, the tick saliva is introduced into the bite wound which has anesthetizing and tissue-liquefying properties. In a second stage, blood and tissue constituents are sucked in. In this stage, the contents of the midgut which may contain pathogens, particularly borrelias, are often regurgitated into the bite wound. Thus, the transmission of the pathogen does not take place until human cell constituents have been sucked in, so that a higher transmission risk can be assumed if human nucleic acids are present in the tick. This connection is supported by animal-experimental investigations which show a clear relation between suction period of the ticks and the transmission frequency of the pathogen. Only if the tick can suck blood for a sufficient time, it is also found in the tick body, and a long period of stay of the tick at the host also increases the risk of pathogen transmission.

After collecting nucleic acid, particularly DNA, from an arthropod, particularly a tick, which was removed from a host, it is used in a PCR reaction. In this connection, it is possible, in a first PCR reaction, to initially use a primer system for the arthropod-borne pathogens, particularly *Borrelia burgdorferi*, and in a subsequent PCR reaction, to employ a primer system for a host-specific gene, e.g. for a human gene, especially c-myc oncogene or actin gene. However, there is also the possibility of carrying out the amplification in a single PCR reaction. The PCR reaction is carried out by means of standard conditions known to a person skilled in the art.

For example, the following primer systems are in consideration for *Borrelia burgdorferi* DNA: JS1 (SEQ ID NO.: 1) (5'-AGAAGTGCTGGAGTCGA-3'), JS2 (SEQ ID NO.: 2) (5'-TAGTGCTCTACCTCTATTAA-3') and FS1 (SEQ ID NO.: 3) (5'-AGTCTGTTTAAAAAGGCA) (Schwartz, J. et al., J. Clin. Microbiol. 30, (1992), 3082–3088).

For example, the following primer systems are in consideration for the DNA of a human c-myc oncogene: o1 (SEQ ID NO.: 4) (5'-CTGGTTTTCCACTACCCGAA-3'), o2 (SEQ ID NO.: 5) (5'-CCGCAACCCTTGCCG-CATCC-3') and o3 (SEQ ID NO.: 6) (5'-GACGCGGGGAGGCTATTCTG-3') (Wolf, J. et al., Cancer Res. 50, (1990), 3095–3100).

Having concluded the PCR reaction, the PCR-amplified DNA is separated e.g. on a 5 to 10% polyacrylamide gel and transferred to a membrane, e.g. nylon membrane. After fixing the DNA to the membrane, it is used in one or more hybridization reactions with radioactively labeled fragments which are specific to either an arthropod-borne pathogen, particularly *Borrelia burgdorferi*, or the host (patient). Having evaluated an applied X-ray film, it can be decided whether the arthropod who bit the host (patient) included human DNA and the DNA of a pathogen. In case both sequences were detectable in the arthropod, an antibiotic treatment should be started prophylatically. This means that it is only necessary to treat patients with a disease risk but not all those bitten by an arthropod. This is a major advantage as regards the costs and stress for the patient.

A kit for carrying out the above processes is also provided according to the invention. In particular, this is a kit for a PCR method, the kit preferably containing primers for human nucleic acid, particularly DNA, more preferably for the DNA of a c-myc oncogene, and primers for *Borrelia burgdorferi* nucleic acid, particularly DNA, as well as buffers, enzymes and carriers, all suited to carry out a PCR. It is especially preferred for the kit to contain the above-mentioned primer systems.

The invention is explained in more detail below by means of an example.

EXAMPLE

Detection of *Borrelia Burgdorferi* DNA and Human DNA in Ticks 22 ticks which had bitten human beings were investigated. A polymerase chain reaction was carried out to detect *Borrelia burgdorferi* DNA and human DNA in ticks by using a primer system for *Borrelia burgdorferi* and a primer system for the human c-myc oncogene. The oligonucleotides for *Borrelia burgdorferi* were: JS1 (SEQ ID NO.: 1) (5'-AGAAGTGCTGGAGTCGA-3'), JS2 (SEQ ID NO.: 2) (5'-TAGTGCTCTACCTCTATTAA-3') and FS1 (SEQ ID NO.: 3) (5'-AGTCTGTTTAAAAAGGCA-3'). Those for the c-myc oncogene were: o1 (SEQ ID NO.: 4) (5'-CTGGTTTTCCACTACCCGAA-3'), o2 (SEQ ID NO.: 5) (5'-CCGCAACCCTTGCCGCATCC-3') and o3 (SEQ ID NO.: 6) (5'-GACGCGGGGAGGCTATTCTG-3'). In this connection, the conditions previously published for patients' urine specimens were applied to the amplification by means of PCR and the detection of the PCR products (cf. Maiwald et al., BIOforum 17, (1994), 232–237).

100 µl of PCR batch included 50 mM KCl, 50 mM Tris (pH 9), 2.0 mM $MgCl_2$, 200 µM dNTPs (deoxynucleoside triphosphate), 500 nM of each primer and 2.5 units of Taq polymerase (AmpliTaq® DNA polymerase, Perkin-Elmer, Norwalk, Conn., U.S.A.), as well as 70 µl of mineral oil. 10 µl were chosen as sample volume. The ticks were processed for PCR by dividing them by means of a scalpel, placing them in a 1.5 ml reaction vessel where they were crushed by means of a pestle (Kontres Instruments, U.S.A.) and then boiling them with 30 µl of a 20% Chelex suspension (BioRad, U.S.A) for 10 min. 10 µl of the supernatant of the Chelex resin were used in the PCR reaction.

For the detection of the PCR products, 30 µl from the PCR reaction batches were separated by means of electrophoresis on 8% polyacrylamide gels (with TBE buffer: 0.089 M Tris, 0.089 M boric acid, 0.002 M EDTA) at 12 V $cm^{-1}$ for 2 to 3 h, and thereafter the gels were stained using ethidium bromide and photographed on a U.V. transilluminator. For the subsequent hybridization, the DNA in the gel was denatured for 15 min. (0.2 M NaOH, 0.6 M NaCl), and thereafter neutralized in 25 mM sodium phosphate buffer (pH 7.0) for 2×15 min. Then, the DNA was transferred from the gel onto a nylon membrane (Sartolon, 0.2 µm pore size, company of Sartorius) by means of electroblot in TBE buffer at 110 mA overnight.

Following the heat fixation of the DNA on the membrane (80° C., 2 h), the membrane was prehybridized at 47° C. for at least 2 h (in 0.9 M NaCl, 6 mM EDTA, 90 mM Tris, 1% SDS with 1 g/l yeast RNA) and then hybridized at 47° C. overnight with the oligonucleotide FS 1 (specific to *Borrelia burgdorferi*, see above) labeled with $^{32}P$ by kinase reaction (Sambrook et al., Molecular cloning: A laboratory manual, $2^{nd}$ ed., Cold Spring Harbor Laboratory Press, Cold Spring Harbor, N.Y., (1989)) in 10 ml of the prehybridization solution. The nylon membrane was then washed in a solution comprising 3×SSC (20×SSC is 3 M NaCl, 300 mM sodium citrate, pH 7.2), 5% SDS and 10 mM sodium phosphate (pH 7.0) at 47° C. for 10 min., then washed again in 1×SSC, 1% SDS at 47° C. for 10 min. and thereafter exposed on an X-ray film (X-OMAT AR, Kodak, U.S.A.) in a cassette.

Six ticks were identified which had *Borrelia burgdorferi* DNA and human DNA. Three of the corresponding six patients developed a Lyme disease according to clinical and serological criteria. Thus, the detection of *Borrelia burgdorferi* DNA together with human DNA in ticks proves suitable to limit the group of people endangered by an infection.

A further collective of 71 ticks which had attached to patients by suction and whose suction period was recorded, were investigated for the presence of the human c-myc gene by means of the above-described PCR method. The $^{32}$P-labeled oligonucleotide o3 (specific to human c-myc oncogene; see above) was used as hybridization sample for the hybridization reaction. As a function of the suction period, the following results showed: (1) suction period 0 to 4 h: 3 of 13 ticks positive (i.e. human DNA could be detected in the tick); (2) 5 to 12 h: 2 of 11 ticks positive; (3) 13 to 24 h: 2 to 18 ticks positive; (4) 25 to 48 h: 8 of 19 ticks positive; (5) over 48 h: 3 to 5 ticks positive. Thus, it could be shown that the probability of the presence of human DNA in ticks increases in a statistically significant manner with increasing suction period of the ticks.

We claim:

1. A process for recognizing a host individual's risk of falling ill after a bite or prick by an arthropod, comprising testing said arthropod for the presence of nucleic acids of the host and of a pathogen transmissible by said arthropod, wherein detecting the presence of both nucleic acids indicates a risk of illness in the host individual.

2. The process according to claim 1, wherein the nucleic acid is DNA.

3. The process according to claim 1, wherein the nucleic acid from the host and that of the pathogen are detected by means of PCR.

4. The process according to claim 1, wherein the arthropod is a tick or mosquito.

5. The process according to claim 1, wherein the arthropod-borne pathogen is a virus, bacteria, protozoa or worm.

6. The process according to claim 1, wherein the pathogen is *Borrelia burgdorferi*.

7. The process according to claim 6, wherein the nucleic acid from the host and that of the pathogen are detected by means of PCR and the PCR uses primers for *Borrelia burgdorferi* to amplify the nucleic acid of the pathogen.

8. The process according to claim 7, wherein the primers have the following sequences (SEQ ID NOS.: 1–3):

JS1: 5'-AGAAGTGCTGGAGTCGA-3',

JS2: 5'-TAGTGCTCTACCTCTATTAA-3', and/or

FS1: 5'-AGTCTGTTTAAAAAGGCA-3'.

9. The process according to claim 1, wherein the host is a human being.

10. The process according to claim 1, wherein the nucleic acid from the host and that of the pathogen are detected by means of PCR and PCR uses primers for human c-myc oncogene to amplify the host nucleic acid.

11. The process according to claim 10, wherein the primers have the following sequences (SEQ ID NOS.: 4–6):

o1: 5'-CTGGTTTTCCACTACCCGAA-3', o2: 5'-CCGCAACCCTTGCCGCATCC, and/or o3: 5'-GACGCGGGGAGGCTATTCTG-3'.

12. A kit for carrying out the process according to claim 2, comprising primers for human DNA, and those for *Borrelia burgdorferi* DNA as well as buffers, enzymes and carriers, which are necessary to carry out PCR.

13. The kit according to claim 12, wherein said primers for human DNA are for the d-myc oncogene.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Borrelia burgdorferi

<400> SEQUENCE: 1
agaagtgctg gagtcga                                                17

<210> SEQ ID NO 2
<211> LENGTH: 20
<212> TYPE: DNA
<213> ORGANISM: Borrelia burgdorferi

<400> SEQUENCE: 2
tagtgctcta cctctattaa                                             20

<210> SEQ ID NO 3
<211> LENGTH: 18
<212> TYPE: DNA
<213> ORGANISM: Borrelia burgdorferi

<400> SEQUENCE: 3
agtctgttta aaaaggca                                               18

<210> SEQ ID NO 4
<211> LENGTH: 20
<212> TYPE: DNA
<213> ORGANISM: Human

<400> SEQUENCE: 4
ctggttttcc actacccgaa                                             20

<210> SEQ ID NO 5
<211> LENGTH: 20
<212> TYPE: DNA
<213> ORGANISM: Human

<400> SEQUENCE: 5
ccgcaaccct tgccgcatcc                                             20

<210> SEQ ID NO 6
<211> LENGTH: 20

```
<212> TYPE: DNA
<213> ORGANISM: Human

<400> SEQUENCE: 6
gacgcgggga ggctattctg                                              20
```